United States Patent
McCormick et al.

[11] Patent Number: 5,824,553
[45] Date of Patent: Oct. 20, 1998

[54] DISPOSABLE STERILIZATION TEST PACK FOR EVALUATING STEAM AND ETHYLENE OXIDE STERILIZATION

[75] Inventors: Patrick J. McCormick, Honeoye Falls; James Jay Kaiser, Webster; Paul M. Eckardt, Rochester, all of N.Y.

[73] Assignee: Getinge/Castle, Inc., Rochester, N.Y.

[21] Appl. No.: 193,712

[22] Filed: Feb. 9, 1994

[51] Int. Cl.$^6$ ................................................ C12Q 1/22
[52] U.S. Cl. ........................ 436/1; 422/58; 422/61; 435/31; 435/287.4
[58] Field of Search .................. 435/291, 31, 287.4; 422/58, 61; 436/1

[56] References Cited

U.S. PATENT DOCUMENTS

| | | |
|---|---|---|
| 3,996,802 | 12/1976 | Smith . |
| 4,486,387 | 12/1984 | Augurt . |
| 4,528,268 | 7/1985 | Andersen et al. . |
| 4,576,795 | 3/1986 | Bruso . |
| 4,579,715 | 4/1986 | Bruso . |
| 4,591,566 | 5/1986 | Smith . |
| 4,596,696 | 6/1986 | Scoville, Jr. . |
| 4,636,472 | 1/1987 | Bruso . |
| 4,692,307 | 9/1987 | Bruso . |
| 4,699,765 | 10/1987 | Hambleton ................................ 422/57 |
| 4,828,797 | 5/1989 | Zwarun et al. . |
| 4,839,291 | 6/1989 | Welsh et al. . |
| 4,863,867 | 9/1989 | Joyce et al. . |
| 4,902,478 | 2/1990 | Hambletion ................................ 422/56 |
| 4,914,034 | 4/1990 | Welsh et al. . |
| 4,918,003 | 4/1990 | Macaro et al. . |
| 5,066,464 | 11/1991 | Augurt ..................................... 422/58 |
| 5,200,147 | 4/1993 | Augurt ..................................... 422/56 |
| 5,204,062 | 4/1993 | Buglino .................................... 422/56 |
| 5,217,901 | 6/1993 | Dyckman . |
| 5,270,217 | 12/1993 | Dyke ...................................... 436/127 |

FOREIGN PATENT DOCUMENTS 0255229  2/1988  European Pat. Off. .

OTHER PUBLICATIONS

Author unknown, "Good Hospital Practice: Ethylene oxide sterilization and sterility assurance", Association for advancement of Medical Instrumentation, p. 1–29, 1992.

Author unknown, "Good Hospital Practice: Steam Sterilization and Sterility Assurance", Association for the Advancement of Medical Instrumentation, pp. 149–197, 1988.

*Primary Examiner*—Jan Ludlow
*Attorney, Agent, or Firm*—Phillips, Lytle, Hitchcock, Blaine & Huber LLP

[57] ABSTRACT

Structure for evaluating the efficacy of sterilization apparatus using either steam or ethylene oxide as sterilant is disclosed. The structure includes an insert of porous material having a cavity formed therethrough for retaining a biological or chemical indicator. The porous material has homogeneous porosity throughout. The insert of porous material and indicator are enclosed within an outer covering which is relatively impervious to penetration of gases and which provides restricted pathways to air and sterilant. The outer covering is provided with removable portions which are removed when the structure is used to evaluate ethylene oxide sterilization. Removal of the portions enlarges the existing pathways for ingress and egress of gases which may be appropriate in certain efficacy testing.

16 Claims, 3 Drawing Sheets

DISPOSABLE STERILIZATION TEST PACK FOR EVALUATING STEAM AND ETHYLENE OXIDE STERILIZATION

TECHNICAL FIELD

This invention relates generally to evaluating the efficacy of sterilizer apparatus. Specifically, this invention is directed to an improved sterilization test pack.

BACKGROUND

Sterilizer units are used in many industries to treat items with a sterilant, such as heat or chemicals, to sterilize and disinfect those items. To assure that a sterilizer apparatus is operating properly and that items placed within the sterilizer are being completely sterilized, it is necessary to evaluate the efficacy of the sterilizer apparatus on a periodic basis.

Protocols for evaluating steam sterilization and ethylene oxide (EO) sterilization were developed several years ago by the Association for the Advancement of Medical Instrumentation (AAMI), and are well-known. For the routine monitoring of steam sterilization processes, the AAMI steam sterilization test protocol requires precise folding and stacking of a selected number of freshly laundered, reusable huck or absorbent surgical towels. A biological indicator is placed in the approximate geometric center of a packaging structure and a chemical indicator is placed adjacent to the biological indicator. The biological and chemical indicators are then placed in the center of the configuration of folded towels. The pack is completed by taping the folded towels in a manner to yield dimensions of approximately 6"×6"×9" and a density of approximately 11.3 pounds per cubic foot.

For the routine monitoring of ethylene oxide sterilization processes, the AAMI EO sterilization test protocol specifies placement of a biological indicator within the barrel of a plastic syringe (tip guard removed) which is then placed within the folds of a freshly laundered, reusable huck or absorbent surgical towel which is in turn placed within a peel pouch or outer wrapper.

In view of the exacting preparation necessary to construct a testing device under the AAMI protocols, and further in view of the variance in testing results which occur from inconsistent construction of testing devices using the AAMI protocol, efforts have been made to develop pre-formed, and preferably disposable, testing devices. Such testing devices are well-known in the field as "sterilization test packs." Studies have demonstrated that, in addition to the benefit of greater consistency in construction, these testing devices offer significant savings to the user compared with the labor costs involved with assembling the AAMI devices (Caporino, P., 1988 *Journal of Healthcare Material Management*, May/June, pp. 38–42). Test packs have been developed which use chemical indicators or biological indicators, or both, centrally positioned within the test pack materials.

Test packs which use chemical indicators are exemplified by the devices disclosed in U.S. Pat. No. 4,486,387 to Augurt, issued Dec. 4, 1984; U.S. Pat. No. 4,596,696 to Scoville, Jr., issued Jun. 24, 1986; U.S. Pat. No. 4,576,795 to Bruso, issued Mar. 18, 1986; U.S. Pat. No. 4,579,715 to Bruso, issued Apr. 1, 1986; and U.S. Pat. No. 4,692,307 to Bruso, issued Sep. 8, 1987. Test packs which use biological indicators are exemplified by the devices disclosed in U.S. Pat. No. 4,528,268 to Andersen, et al., issued Jul. 9, 1985; U.S. Pat. No. 4,591,566 to Smith, issued May 27, 1986; U.S. Pat. No. 4,828,797 to Zwarun, et al., issued May 9, 1989; U.S. Pat. No. 4,839,291 to Welsh, et al., issued Jun. 13, 1989; and U.S. Pat. No. 4,914,034 to Welsh, et al., issued Apr. 3, 1990.

Test packs have been developed which consist of separate layers of disparate materials held together by a porous overwrap or a box. Intermediate layers of material are formed with a cavity to house a biological indicator within. Examples of such test packs are disclosed in U.S. Pat. No. 4,636,472 to Bruso, issued Jan. 13, 1987; U.S. Pat. No. 4,863,867 to Joyce, et al., issued Sep. 5, 1989; and U.S. Pat. No. 4,918,003 to Macaro, et al., issued Apr. 17, 1990. Because these test pack designs necessitate the use of papers or other materials having various porosities (e.g., non-porous, semi-porous or highly porous, and combinations thereof), and require a particular stacking arrangement, they are difficult and costly to manufacture and assemble. Additionally, access to the biological indicator housed within the materials is more difficult with these designs.

Thus, there remains a need for a test pack useful for evaluating both steam and EO sterilization efficacy which is inexpensively manufactured, easily assembled, and more conveniently used by those in the field.

DISCLOSURE OF THE INVENTION

According to the present invention, disposable structure for evaluating the efficacy of sterilization apparatus is provided which presents an effective challenge to entry of sterilant into the interior of the structure and provides ease of construction and use. The structure provides accurate evaluation of sterilizer efficacy with both steam and ethylene oxide sterilant use. The structure provides sterilizer efficacy evaluation equivalent to the protocols set by the Association for the Advancement of Medical Instrumentation for the routine monitoring of steam and ethylene oxide sterilization processes.

The structure disclosed herein generally comprises an insert of porous material having a cavity formed therein which is sized to receive an indicator for determining sterilant penetration into the structure. The insert is positioned within an outer covering. The insert of porous material has homogeneous porosity and restricts the entry of sterilant into the structure. The porous material may be any material of suitable porosity which provides adequate restriction of sterilant. Such materials may include finer paper, sponge, sintered polymers and the like. The insert may be of one piece construction, such as a thickness of sponge-like material. More typically, the insert may comprise a stack of individual sheets of porous material, such as paper, each one having comparable porosity. Paper having a Gurley porosity ranging from about 25 to about 45 seconds may be particularly suitable.

The porous material is formed with a cavity positioned in the center for retaining an indicator capable of detecting sterilant penetration. The indicator retained in the cavity preferably may be one which is proficient at evaluating both steam sterilization and ethylene oxide sterilization, but may be of a type which is suitable for the evaluation of a single type of sterilant. The indicator may be either a chemical indicator or a biological indicator, or both.

The porous material and indicator are retained within an outer covering which is relatively impermeable to air and sterilants. The outer covering encloses the porous material and indicator in a manner which provides restricted pathways for egress of air and ingress of sterilant. The outer covering may be made of any innately impervious material, such as plastic, or the outer covering may be made of a material which may be contacted with a substance which renders it relatively impervious.

The outer covering is further provided with removable portions which enlarge the pre-existing pathways for sterilant entry when the structure is being used to evaluate sterilization using ethylene oxide. Such removable portions may be provided in the form of at least one removable end flap, or in the form of removable tabs. The outer covering is constructed so that various numbers and combinations of removable portions may be removed to provide varying degrees of permeability to the outer covering. The porous material insert and the outer covering having variable removable portions provides a tortuous pathway through which sterilant must pass in order to contact the indicator within the cavity.

The use of a single portion of homogeneously porous material provides economical manufacture and ease of construction and assembly of the structure thereby presenting a significant improvement over similar structures in the field. The simplified structure of the porous material is made possible by the configuration of the impervious outer covering which provides limited access of sterilant to the interior of the structure.

BRIEF DESCRIPTION OF THE DRAWINGS

In the drawings, which illustrate what is currently regarded as the best mode for carrying out the invention.

DESCRIPTION OF THE ILLUSTRATED EMBODIMENTS

Structure of the Illustrated Embodiment

Figure 1:
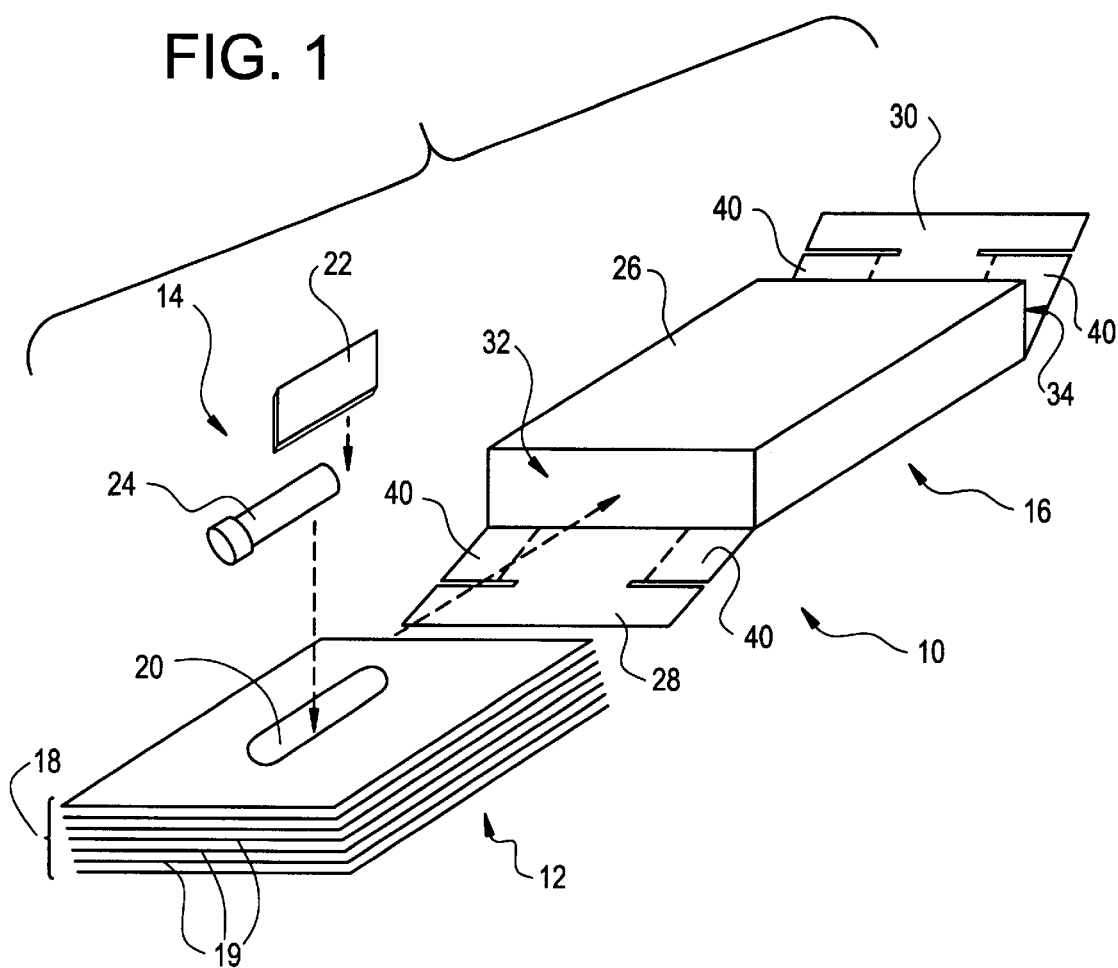
FIG. 1 is an exploded perspective view of the structure in disassembled form.

As shown by FIG. 1, the disposable test pack structure 10 of the present invention generally includes an insert of porous material 12, an indicator 14 for determining sterilant penetration, and an outer covering 16 of relatively impermeable material which encloses the porous material 12 and indicator 14.

Figure 2:
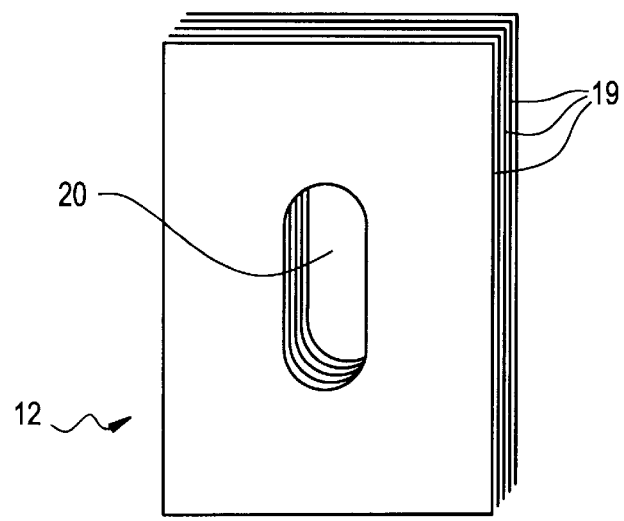
FIG. 2 is a perspective view of the porous insert of the structure shown by FIG. 1.

The porous material insert 12, as shown by FIG. 1, is a stack 18 of individual sheets of paper, each sheet 19 having a porosity comparable to each other sheet 19 such that the insert 12 as a whole has a homogeneous porosity. Each sheet 19 of the insert 12 is cut with a hole in the center. When the sheets 19 are stacked together, a cavity 20 is formed in the center of the porous material insert 12 by alignment of the holes, as shown by FIG. 2.

An indicator 14 is positioned within the cavity 20 where access is restricted by the porous material insert 12. The indicator 14 may preferably be one which is proficient at evaluating both steam sterilization and ethylene oxide sterilization, but may be an indicator 14 of the type which can evaluate only a single type of sterilant. Both a chemical indicator 22 and a biological indicator 24 are shown by FIG. 1; however, a single indicator may be used instead.

The porous material insert 12 and indicator 14 are enclosed within an outer covering 16 which is relatively impermeable to penetration of gases. That is, the outer covering may be constructed of an innately impervious material such as plastic; or, alternatively, the material may be of a type which retains the quality of being impermeable during normal use in a sterilizer, but which may become less impermeable following extended exposure to heat or moisture. The outer covering 16, shown by FIG. 1, is a box 26 constructed of sturdy material, such as paperboard stock, coated with a material which renders the paperboard relatively impermeable to air and sterilant. Such coatings include plastic sheeting, resinous or waxy substances, or the like.

The particular dimensions of the outer covering 16 may vary. Dimensions of one-half inch high by four and one-half inches long by two and one-half inches wide (0.5"h×4.5"1× 2.5" w) are very suitable for the outer covering 16 when used in most testing applications and most sterilizers. Variation in the dimensions of the outer covering 16, and thus the amount of porous material 12 therewithin, will modify the ability of sterilant to enter into the test pack.

The outer covering 16 is constructed to provide openings through which air may exit the interior of the test pack 10 and through which sterilant may enter to reach the inner cavity 18. In the embodiment shown by FIG. 1, the box 26 includes end flaps 28 and 30 which fold and insert into the box 26 to obstruct the open ends 32 and 34 thereof. Thus, small gaps 36 formed at the insertion point of the end flaps 28 and 30 create restricted pathways for air and sterilant travel, as illustrated by FIG. 3.

Figure 3:
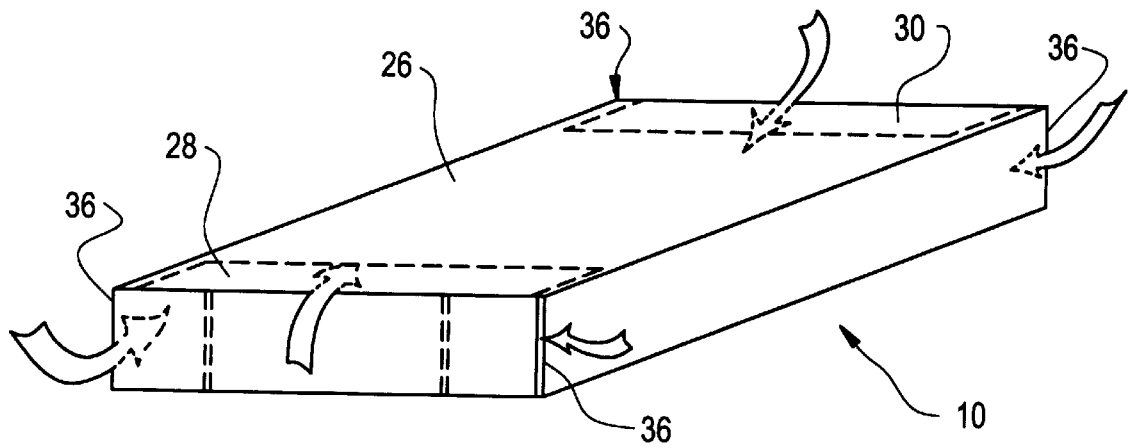
FIG. 3 is a perspective view of the structure shown by FIG. 1 configured for evaluating steam sterilization, some portions being shown in phantom.
Figure 4:
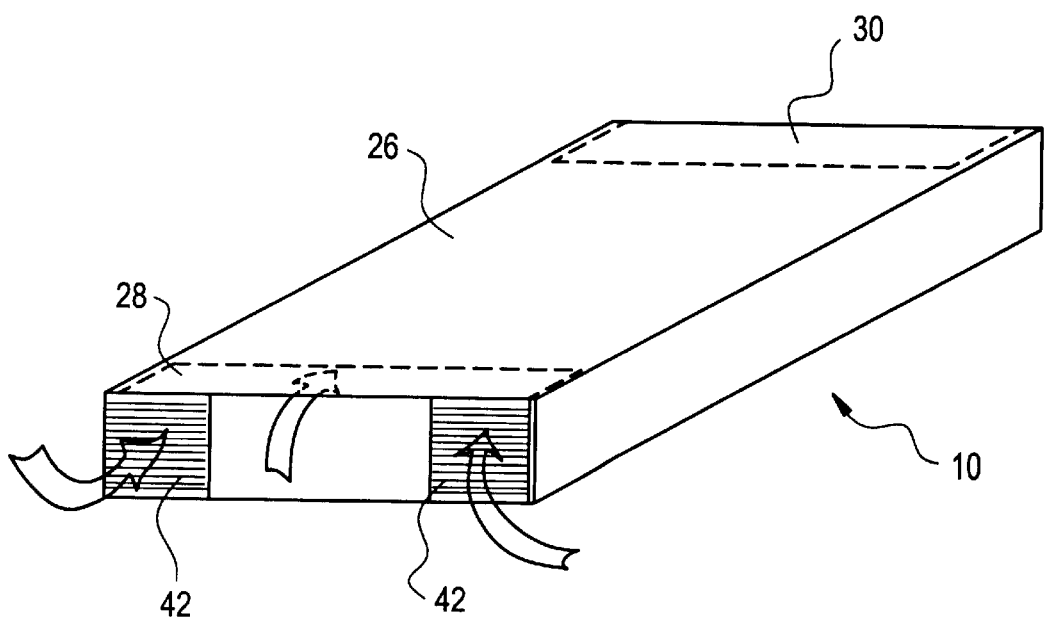
FIG. 4 is a perspective view of the, structure shown by FIG. 1 configured for evaluating ethylene oxide sterilization, some portions being shown in phantom.

When the test pack 10 is used to evaluate steam sterilization, the end flaps 28 and 30 are folded and inserted into the structure as illustrated by FIG. 3. Sterilant enters into the outer covering 16 as indicated by the enlarged arrows. When the test pack 10 is used to evaluate ethylene oxide sterilization, the perforated tabs 40, shown by FIGS. 1 and 3, are removed to enlarge the existing entryway for passage of sterilant into the interior of the test pack 10. As illustrated by FIG. 4, removal of the tabs 40 exposes the edge 42 of the porous material insert 12 and provides increased entry of sterilant.

The box 26 may be configured with foldable end flaps 28 and 30 at opposing ends of the box 26, as illustrated by FIG. 1. Alternatively, the box 26 may be configured with a single foldable end flap. The box 26 is configured with a plurality of tabs 40, typically four, any or all of which may be removed to enlarge the existing entryway for passage of sterilant in ethylene oxide sterilization evaluation.

Figure 5:
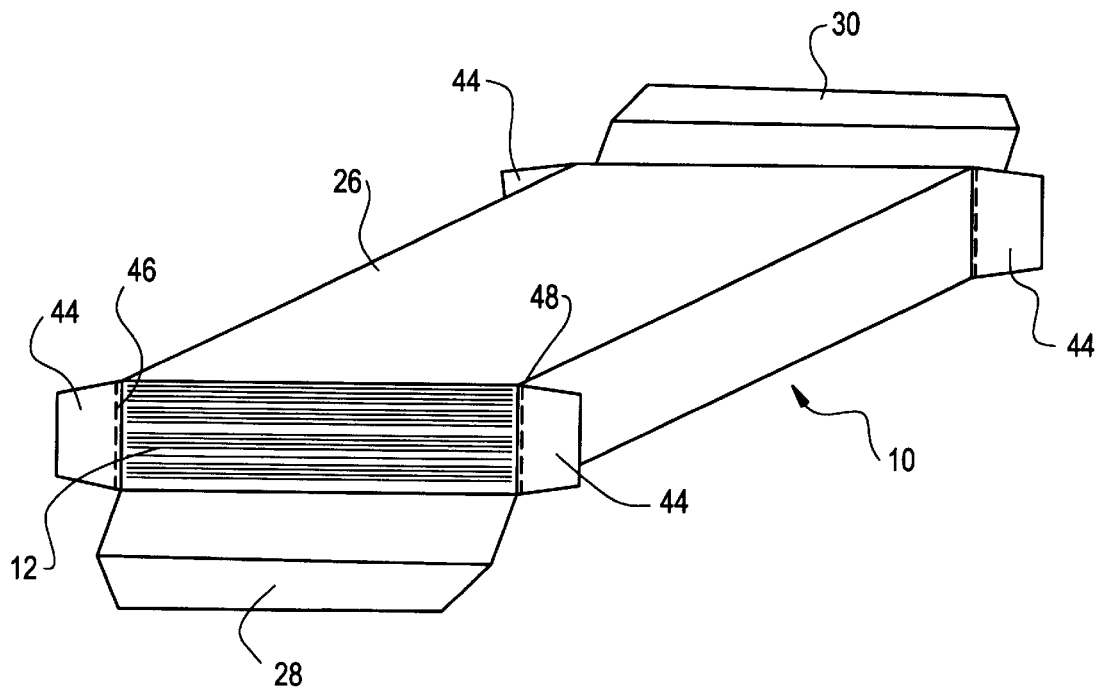
FIG. 5 is a perspective view illustrating an alternative embodiment of the structure.
Figure 6:
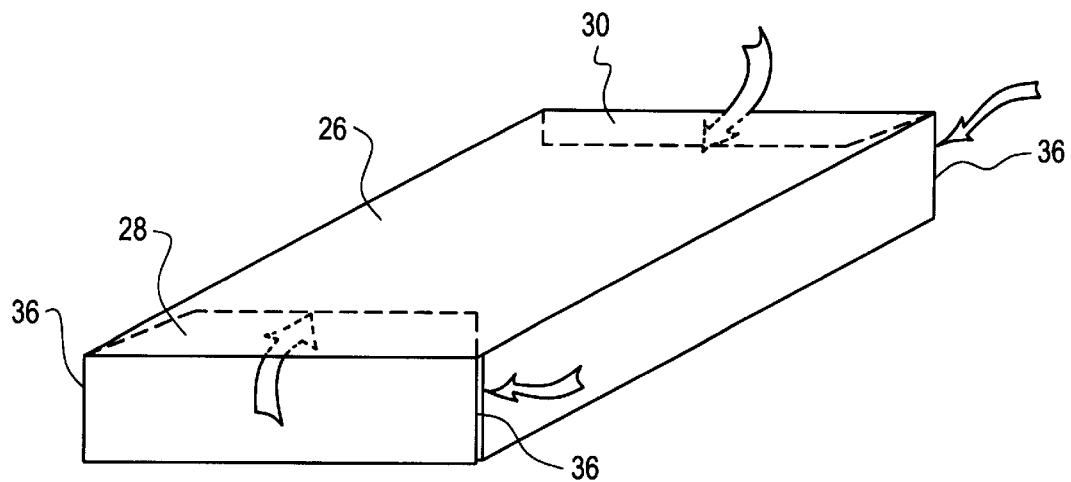
FIG. 6 is a perspective view of the structure shown by FIG. 5, configured for evaluating ethylene oxide sterilization, some portions being shown in phantom.

In an alternative embodiment illustrated by FIGS. 5 and 6, the box 26 is constructed with tabs 44 which are connected to the outer edges 46 and 48 of the box 26 and are foldable inwardly. When the test pack 10 is used in evaluating steam sterilization, the tabs 42 are folded in, and the end flaps 28 and 30 are folded and inserted as described previously. Air and steam must then travel a more tortuous route around the tabs 44 to exit or enter between the end flaps 28 and 30 and the tabs 44. When the test pack 10 is used to evaluate ethylene oxide sterilization, the tabs 44 are removed prior to folding and inserting the end flaps 28 and 30 into the box 26. Thus, an enlarged opening 36, creating a less tortuous pathway, is provided for entry of sterilant into the test pack 10, as illustrated by FIG. 6.

Test Pack Standards Established by AAMI

The porosity of the filer paper or other porous material used in the invention should be such that the performance of the test pack is comparable to that of the corresponding AAMI test pack. Results of a study published by the AAMI regarding the development and qualification of the 16-Towel Biological-Indicator Challenge Test Pack (herein referred to as the 16-Towel Test Pack) for routine monitoring of steam sterilization suggest that when processed under gravity steam sterilization conditions, biological indicators placed within the 16-Towel Test Pack should survive 15–16 minutes exposure at 250° F., and be completely inactivated after 25 minutes exposure to the same conditions (Table E2. Appendix E. AAMI SSSA-1988. "Good Hospital Practice: Steam Sterilization and Sterility Assurance. AAMI Standards and Recommended Practices." Volume 1: Sterilization, Association for the Advancement of Medical Instrumentation. 3330 Washington Blvd. Suite 400. Arlington, Va. 22201). When processed under deep vacuum conditions at 270° F., biological indicators placed within the 16-Towel pack should survive processing of 0 minutes exposure, the time required for the sterilizer to reach its temperature setpoint, and be completely inactivated after 4 minutes exposure to the same conditions (Table E3,- ibid).

Similar data has been published recently by the AAMI regarding the resistance performance characteristics of the AAMI Routine Test Pack for ethylene oxide sterilization. The test pack used by the AAMI for EO sterilization comprised a biological indicator placed within a 20 milliliter plastic syringe (with the plunger inserted and the needle and needle guard removed) which in turn was placed in a single 100-percent cotton surgical towel, folded in thirds lengthwise and then in thirds widthwise to produce nine layers of folds. The folded towel was then placed in a 7 inch by 13 inch paper/film pouch and was sealed. The AAMI test packs were tested in BIER (biological indicator-evaluator resistometer) ethylene oxide exposure vessels. The AAMI tests suggest that the mean kill time for biological indicators placed in EO test packs averages 41.6±11.9 minutes when processed in an EO BIER vessel under conditions of 600 mg/L EO, 60±10% relative humidity and 54°±1° C. (Table A.1, Annex A. Biological Indicator Test Packs. ANSI/AAMI ST41-1992 Good Hospital Practice: Ethylene Oxide Sterilization and Sterility Assurance.).

Test Data of a Typical Embodiment

To determine the effect of the porosity of the filler paper on the performance of the present test pack invention under steam sterilization conditions, testing was conducted with filler paper of various porosities as described in Table I. Each test pack tested was assembled as illustrated in FIG. 1 with inserts comprised of filler paper sheets each having the same porosity, those porosities being noted in Table I. For each test pack, a number of sheets were placed in the stack to produce the dimensions of 0.5 inches high by 4.5 inches long by 2.5 inches wide. Thus, for sheets with a Gurley porosity of 25 to 45 seconds, approximately 65 sheets were used; for sheets having a Gurley porosity of 10–20 seconds, approximately 110 sheets were used; and for sheets having a Gurley porosity of 60–70, approximately 127 sheets were used. A commercially available self-contained biological indicator was employed to determine the effect of the filler paper of different porosities on the resistance performance of the test pack of the present invention. The data in Table I is presented as the number of biological indicators which were positive for growth per number of test packs of the present invention tested.

TABLE I

Effect of Filler Paper of Varying Porosity On the Resistance Performance of Test Packs Processed by Steam Sterilization

| Temp | cycle type** | exposure | 10–20 sec | Porosity* 25-45 sec | 60–70 sec |
|---|---|---|---|---|---|
| 121 C. | gravity | 12 min | 10/10 | 10/10 | 10/10 |
| 121 C. | " | 15 min | 10/10 | 10/10 | 10/10 |
| 121 C. | " | 17 min | 10/10 | 10/10 | 10/10 |
| 121 C. | " | 20 min | 8/10 | 2/10 | 10/10 |
| 121 C. | " | 22 min | 4/10 | 0/10 | 10/10 |
| 121 C. | " | 30 min | 0/10 | 0/10 | 9/10 |
| 121 C. | " | 35 min | 0/10 | 0/10 | 0/10 |
| 121 C. | " | 40 min | 0/10 | 0/10 | 0/10 |
| 132 C. | deep | 0 min | 10/10 | 10/10 | 10/10 |
| 132 C. | vacuum | 0.5 min | 4/10 | 8/10 | 10/10 |
| 132 C. |  | 1 min | 0/10 | 1/10 | 8/10 |
| 132 C. |  | 4 min | 0/10 | 0/10 | 0/10 |

*Porosity in Gurley seconds according to TAPPI method T460 os-68 Air Resistance of Paper.
**Cycle type: gravity = no prevacuum deep vacuum = single prevacuum to 28" Hg.
Testing conducted in a 26" × 62" × 72" steam sterilizer.

To evaluate the effectiveness of filler papers of varying porosities on the resistance performance of the present test pack invention under ethylene oxide sterilization conditions, testing was conducted as indicated in Table II. The evaluated test packs were assembled as illustrated in FIG. 1 with inserts having homogeneously porous filler papers of the porosities noted in Table II. Test packs constructed of filler paper having a Gurley porosity of 25–45 seconds contained approximately 65 sheets per stack; test packs constructed of filer paper having a Gurley porosity of 10–20 seconds contained approximately 110 sheets per stack; and test packs constructed of filler paper having a Gurley porosity of 60–70 seconds contained approximately 127 sheets. Each test pack had the dimensions of 0.5 inches high by 4.5 inches long by 2.5 inches wide. A commercially available self-contained biological indicator was employed to determine the effect of the filler paper of different porosities on the resistance performance of the test pack. The data in Table II is presented as the number of biological indicators positive for growth per number of test packs of the present invention tested.

TABLE II

Effect of Filler Paper of Varying Porosity On the Resistance Performance of Test Packs Processed by Ethylene oxide Sterilization

| temp | cycle type** | exposure | 10–20 sec | Porosity* 25–45 sec | 60–70 sec |
|---|---|---|---|---|---|
| 55 C. | 600 mg/L EO | 20 min | 10/10 | 10/10 | 10/10 |
| " | " | 25 min | 4/10 | 10/10 | 10/10 |
| " | " | 30 min | 1/10 | 7/10 | 7/10 |
| " | " | 35 min | 0/10 | 0/10 | 2/10 |
| " | " | 40 min | 0/10 | 1/10 | 0/10 |
| " | " | 60 min | 0/10 | 0/10 | 0/10 |

*Porosity in Gurley seconds according to TAPPI method T460 os-68 Air Resistance of Paper.
**Testing conducted in a Joslyn EO BIER vessel with 600 mg/L EO and 50 ± 10% relative humidity.

Based on the data shown in Table I and Table II, filler papers with a Gurley porosity range of 25–45 seconds are preferred to allow acceptable resistance performance with both steam and ethylene oxide sterilization. Filler papers with Gurley porosity values exceeding 45 seconds may lead to survival of the biological indicator within the test pack in excess of 25 minutes exposure under steam 121° C. gravity sterilization conditions (Table I). Filler papers with Gurley porosity values less than 25 seconds may lead to premature inactivation of the biological indicator under ethylene oxide sterilization processing conditions.

The number of sheets in the test pack of the invention will affect the performance of the test pack. That is, too few sheets allow a greater amount of sterilant to enter thereby leading to early inactivation of the biological indicator, while too many sheets prevent entry of a sufficient amount of sterilant to inactivate the biological indicator. The effect of varying numbers of sheets in the test pack of the invention is demonstrated in Table III.

The test packs used in developing the data shown in Table III were constructed as shown by FIG. 1 and had the approximate dimensions of 0.5 inches high by 4.5 inches long by 2.5 inches wide. Each test pack was constructed using sheets having a Gurley porosity of 25–45 seconds, and the test packs contained either 45, 55, 65 or 70 sheets. Testing was done in a steam BIER sterilizer or EO BIER sterilizer as indicated. From the data in Table m, it has been determined that approximately 65 sheets of Gurley porosity 25–45 seconds provides an appropriate inactivation of the biological indicator.

TABLE III

| | | Number of Filler Sheets Per Pack | | | |
|---|---|---|---|---|---|
| Condition | Exposure | 45 | 55 | 65 | 70 |
| 121.1 C. gravity (steam) | 12 min. | 10/10 | 10/10 | 10/10 | 10/10 |
| 121.1 C. gravity (steam) | 15 min. | 7/10 | 9/10 | 10/10 | 7/10 |
| 121.1 C. gravity (steam) | 17 min. | 0/10 | 0/10 | 5/10 | 0/10 |
| 121.1 C. gravity (steam) | 20 min. | 0/10 | 0/10 | 1/10 | 0/10 |
| 121.1 C. gravity (steam) | 30 min. | 0/10 | 0/10 | 0/10 | 0/10 |
| 132.2 C. prevacuum (steam) | 2 min. | 8/10 | 6/10 | 10/10 | 9/10 |
| 132.2 C. prevacuum (steam) | 4 min. | 3/10 | 0/10 | 7/10 | 2/10 |
| 132.2 C. prevacuum (steam) | 6 min. | 0/10 | 0/10 | 0/10 | 0/10 |
| 132.2 C. prevacuum (steam) | 8 min. | 0/10 | 0/10 | 0/10 | 0/10 |
| 600 mg/L EO | 20 min. | 5/10 | 10/10 | 10/10 | 10/10 |
| " | 25 min. | 3/10 | 4/10 | 10/10 | 10/10 |
| " | 30 min. | 0/10 | 0/10 | 10/10 | 10/10 |
| " | 60 min. | 0/10 | 0/10 | 0/10 | 0/10 |

Removal of tabs 40 from box 26 allows more gas or sterilant into the test pack invention. Removal of one or more tabs may be appropriate in certain types of sterilization, such as EO sterilization. The relationship between sterilization efficacy and the removal of varying numbers of tabs 40 from the box 26 is demonstrated in Table IV.

TABLE IV

Effect of the Number of Tabs Removed On the Resistance Performance of Test Packs Processed by Ethylene Oxide Sterilization

| temp | cycle type* | exposure | 0 | 1 | 2 | 3 | 4 |
|---|---|---|---|---|---|---|---|
| 55c | 600 mg/L EO | 20 min | 10/10 | 10/10 | 10/10 | 10/10 | 10/10 |
| | | 30 min | 10/10 | 10/10 | 10/10 | 5/10 | 7/10 |
| | | 40 min | 10/10 | 6/10 | 2/10 | 1/10 | 0/10 |
| | | 50 min | 4/10 | 0/10 | 0/10 | 0/10 | 0/10 |
| | | 60 min | 2/10 | 0/10 | 0/10 | 0/10 | 0/10 |

*Testing conducted in a Joslyn EO BIER vessel at 50 ± 10% relative humidity.

The data in Table IV is presented as the number of biological indicators positive for growth per number of test packs of the present invention tested. Test packs were assembled as illustrated in FIG. 1 with filler paper having a Gurley porosity of 25–45 seconds. A commercially available self-contained biological indicator was employed to determine the effect of the number of tabs removed on the resistance performance of the test pack. The data in Table IV demonstrates that inactivation of the biological indicator increases with the number of tabs removed.

The construction of the present invention is greatly simplified over prior test pack constructions. The single insert of homogeneously porous material eliminates the costly and time-consuming assembly of multiple layers of dissimilar materials characteristic of prior art test packs. The single insert construction also provides easy access to the indicator after the sterilization cycle has been completed.

Reference herein to specific details of the illustrated embodiments is not intended to limit the scope of the claims which recite those features regarded as important to the invention and are intended to define the embodiments illustrated and their equivalents.

What is claimed is:

1. Structure for evaluating the efficacy of sterilization comprising:

an indicator;

an insert of porous material having homogeneous porosity and a defined thickness of material;

a cavity formed through said thickness of material of said insert, said cavity being sized to receive said indicator therein; and an outer covering of material rendered impervious to penetration of gases, said outer covering providing restricted pathways for entry of gases and having removable portions in combination with said pathways.

2. The structure of claim 1 wherein said insert of porous material comprises individual sheets of paper stacked together, each sheet being uniformly sized and of similar porosity to each other sheet.

3. The structure of claim 2 wherein said porosity of said individual sheets is between about a Gurley porosity of 25 and about a Gurley porosity of 45.

4. The structure of claim 2 wherein said outer covering is a box having a positionable end flap.

5. The structure of claim 4 wherein said removable portions are combined with said positionable end flap.

6. The structure of claim 4 wherein said box is coated with a substance to render said box impervious to penetration of gases.

7. The structure of claim 4 wherein said indicator is a biological indicator.

8. The structure of claim 1 wherein said indicator is a chemical indicator.

9. A disposable test pack for evaluating the efficacy of sterilization apparatus comprising:

a biological indicator;

an insert of porous material having a defined thickness of material and a cavity formed through said thickness sized to receive said biological indicator, said porous material having homogeneous porosity; and an outer covering sized to enclose said insert of porous material, said outer covering being of material rendered impervious to air and sterilant and configured to provide restricted pathways having removable tabs in combination with said pathways.

10. The disposable test pack of claim 9 wherein said insert has a Gurley porosity of from between 25 to 45.

11. The disposable test pack of claim 10 wherein said insert of porous material comprises sheets of paper stacked together, each sheet having similar porosity of each other sheet.

12. The disposable test pack of claim 10 wherein said outer covering is a box having six sides, each side being contacted with a material rendering said box impervious to air and sterilant.

13. A method of evaluating sterilization efficacy comprising:

providing structure for evaluating sterilization efficacy, said structure including an indicator centrally positioned within a porous member having homogeneous porosity and having a cavity formed through the thickness of said porous member for retaining said indicator and restricting access thereto and an outer covering enclosing said porous member and said indicator, said outer covering being of material rendered impervious to penetration of gases, providing restricted pathways for passage of gases, and having removable portions for enlarging said pathways;

placing said structure into a sterilizer apparatus;

cycling said sterilizer apparatus;

removing said structure from said sterilizer following said cycling; and processing said indicator to evaluate sterilization.

14. The method according to claim 13 wherein said indicator is a biological indicator.

15. The method according to claim 14 wherein said porous member comprises individual sheets of paper stacked together.

16. A method of evaluating sterilization efficacy comprising:

providing structure for evaluating sterilization efficacy, said structure including a biological indicator centrally positioned within a porous member having homogeneous porosity and comprising a stack of individual sheets of paper and a cavity formed therethrough for retaining said indicator, and an outer covering enclosing said porous member and said indicator, said outer covering being of material rendered impervious to penetration of gases, providing restricted pathways for passage of gases, and having removable portions for enlarging said pathways;

removing said removable portions from said structure;

placing said structure into a sterilizer apparatus;

cycling said sterilizer apparatus;

removing said structure from said sterilizer following said cycling; and processing said indicator to evaluate sterilization.

* * * * *